US00PP17143P2

(12) United States Plant Patent
Gitzels

(10) Patent No.: US PP17,143 P2
(45) Date of Patent: Oct. 10, 2006

(54) ***DAHLIA* PLANT NAMED 'DAPARED'**

(50) Latin Name: *Dahlia variabilis*
Varietal Denomination: Dapared

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 1 day.

(21) Appl. No.: 11/168,826

(22) Filed: Jun. 28, 2005

(51) Int. Cl.
*A01H 5/00* (2006.01)

(52) U.S. Cl. ..... Plt./321
(58) Field of Classification Search ..... Plt./321
See application file for complete search history.

*Primary Examiner*—Kent Bell
(74) *Attorney, Agent, or Firm*—Wood, Phillips, Katz, Clark & Mortimer

(57) ABSTRACT

A new and distinct *Dahlia* plant named 'Dapared', characterized by its red-colored ray florets, yellow-colored disc florets, dark green-colored foliage, and compact, upright, and mounded growth habit.

2 Drawing Sheets

Latin name of genus and species of plant claimed: *Dahlia variabilis*.
Variety denomination: 'Dapared'.

BACKGROUND OF THE INVENTION

The present invention relates to a new and distinct *Dahlia* plant botanically known as *Dahlia variabilis* and hereinafter referred to by the cultivar name 'Dapared'.

The new cultivar originated in a controlled breeding program in Rijsenhout, The Netherlands, on Jun. 1, 2000. The objective of the breeding program was the development of freely flowering *Dahlia* cultivars with large flowers and a compact, and upright growth habit.

The male parent of the new cultivar was the commercially available cultivar Connie, U.S. Plant Pat. No. 6,768. 'Connie' is characterized by its red-colored ray florets and compact, upright growth habit. The female parent of the new cultivar was the proprietary breeding selection designated '3323', not patented. '3323' is characterized by its red-colored ray florets, dark green-colored foliage, and compact growth habit. Seed from the above stated cross-pollination was germinated and grown to maturity. One plant within the progeny was discovered and selected by the inventor on Aug. 1, 2001 at Rijsenhout, The Netherlands.

Asexual reproduction of the new cultivar by terminal stem cuttings taken since August 2001 at Rijsenhout, Netherlands and West Chicago, Ill. has demonstrated that the new cultivar reproduces true to type with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment such as temperature, light intensity, and day length without, however, any variance in genotype.

The following characteristics of the new cultivar have been repeatedly observed and can be used to distinguish 'Dapared' as a new and distinct cultivar of *Dahlia* plant:

1. Semi-double flower form.
2. Red-colored ray florets and yellow-colored disc florets.

3. Dark green-colored foliage.
4. Compact, upright, and mounded growth habit.

Plants of the new cultivar differ from plants of the male parent primarily in growth habit and from plants of the female parent in flower size and flower color.

Of the many *Dahlia* cultivars known to the inventor, the most similar to the new cultivar is the male parent 'Connie', U.S. Plant Pat. No. 6,768. However, in side by side comparisons, plants of the new cultivar differ from plants of 'Connie' in the following characteristics:

1. Plants of the new cultivar are more compact than plants of 'Connie'.
2. Plants of the new cultivar exhibit ray florets of a slightly different color than do plants of 'Connie'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of the new cultivar. The plants were grown for 11 weeks in a greenhouse at West Chicago, Ill.

DETAILED BOTANICAL DESCRIPTION

Figure 1:
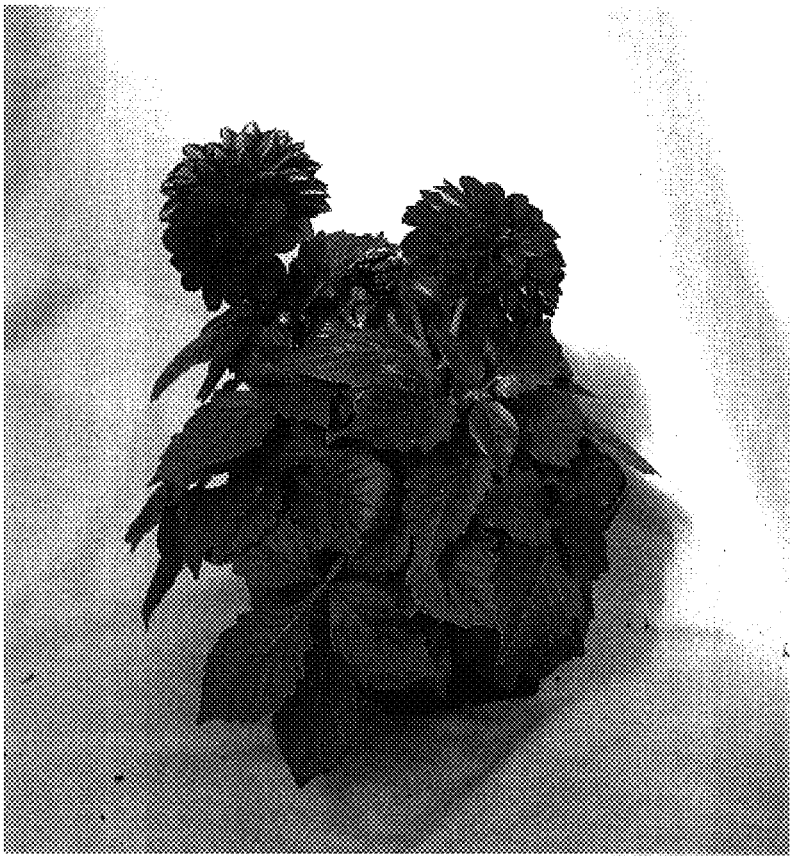
FIG. 1 illustrates a side view of the overall growth and flowering habit of 'Dapared'.
Figure 2:
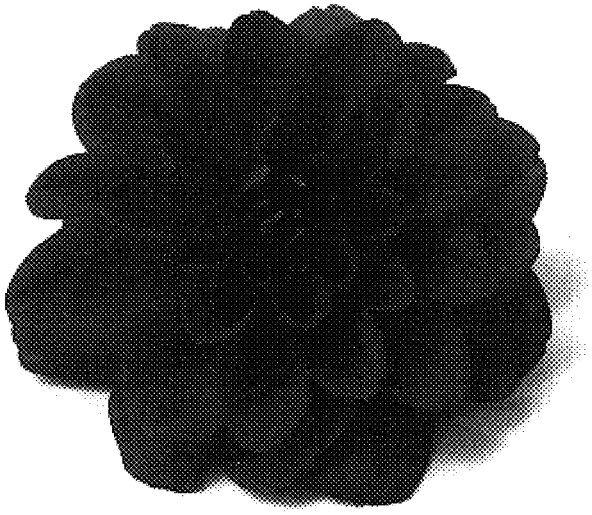
FIG. 2 illustrates a close-up view of a single inflorescence of 'Dapared' with the ray florets just opened.
Figure 3:
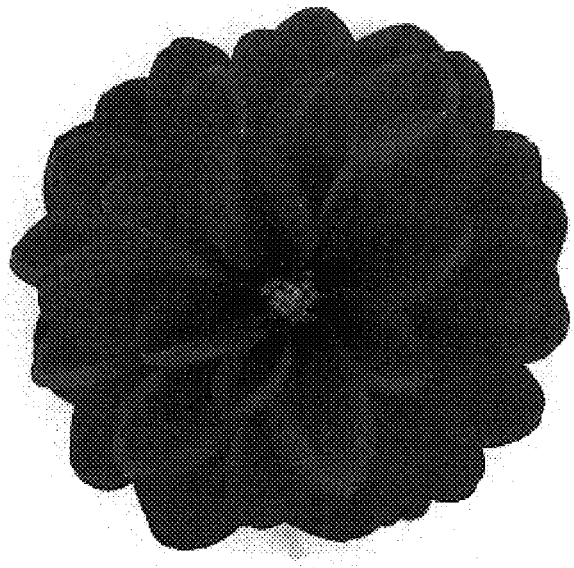
FIG. 3 illustrates a close-up view of a single inflorescence of 'Dapared' with the ray florets fully open and the disc florets unopen.
Figure 4:
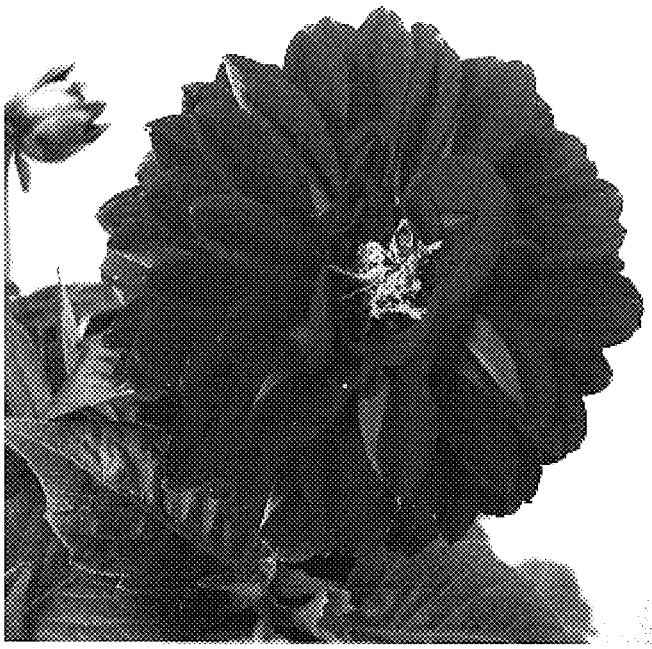
FIG. 4 illustrates a close-up view of a single inflorescence of 'Dapared' with fully open ray florets and fully open disc florets.

The chart used in the identification of colors described herein is The R.H.S. Colour Chart of The Royal Horticultural Society, London, England, 2001 edition, except where general color terms of ordinary significance are used. The color values were determined on Jun. 15, 2005 between 10:00 a.m. and 11:45 a.m. under natural light conditions in West Chicago, Ill.

The following descriptions and measurements describe plants produced from cuttings of stock plants and grown in a double polycarbonate-covered greenhouse under conditions comparable to those used in commercial practice. The plants were grown in 10 cm pots for 11 weeks while utilizing a soil-less growth medium. Greenhouse temperatures were maintained at approximately 65°–75° F. (18°–24° C.) during the day and approximately 60°–65° F. (15°–18° C.) during the night. Greenhouse light levels were maintained at approximately 4,000–6,000 footcandles during the day. Plants were pinched three weeks after planting of rooted cuttings.

Botanical classification: *Dahlia variabilis* cultivar Dapared.

Parentage:

*Male, pollen, parent.*—'Connie', U.S. Plant Pat. No. 6,768.

*Female, seed, parent.*—Proprietary *Dahlia* breeding selection designated '3323', not patented.

Propagation:

*Type cutting.*—Terminal tip.

*Time to initiate roots.*—Approximately 7 to 10 days.

*Time to produce a rooted cutting.*—Approximately 21 to 28 days.

*Rooting habit.*—Freely branching.

*Root description.*—Fine, fibrous.

*Tubers.*—Will form under short day conditions of at least 13 to 14 hours of darkness.

Plant description:

*Crop time.*—Approximately 6–8 weeks.

*Growth habit.*—Basal branching, pinching enhances branching.

*General appearance and form.*—Upright, mounded and vigorous.

*Size.*—Height from top of soil to top of plant plane: Approximately 18 cm. Height from top of soil to top of foliage: Approximately 13 cm. Width/area of spread: Approximately 21.7 cm.

*Branch description.*—Quantity per plant: Approximately 4. Strength: Strong. Length: Approximately 9.6 cm. Diameter: Approximately 6.5 mm. Length of center internode: Approximately 1.1 cm. Texture: Glabrous. Color: Between 144A and 144B.

*Foliage.*—Quantity of leaves per lateral branch: Approximately 11. Type: Simple and compound. Quantity of leaflets per compound leaf: 3. Fragrance: None. Arrangement: Opposite. Aspect: At acute angle to stem at first, becoming downturning with age. Leaf/leaflet: Shape: Ovate. Apex: Acuminate. Base: Obtuse. Margin: Dentate. Venation pattern: Pinnate. Color of upper surface of all leaves/leaflets: Darker than 137A with venation of 145B. Color of lower surface of all leaves/leaflets: Lighter than N138B with venation of 145D. Texture of upper and lower surface of all leaves/leaflets: Sparse pubescence, denser along veins. Length of simple leaf: Approximately 7.0 cm. Width of simple leaf: Approximately 5.4 cm. Length of petiole of simple leaf: Approximately 3.1 cm. Diameter of petiole of simple leaf: Approximately 3.3 mm. Texture of petiole of simple leaf: Glabrous. Color of petiole of simple leaf: Between 145B and 145C. Length of mature trifoliate leaf: Approximately 7.3 cm. Width of mature trifoliate leaf: Approximately 9.4 cm. Length of petiole of mature trifoliate leaf: Approximately 3.8 cm. Diameter of petiole of mature trifoliate leaf: Approximately 3.5 mm. Texture of petiole of mature trifoliate leaf: Glabrous. Color of petiole of mature trifoliate leaf: Between 145B and 145C with 187A where leaflets are attached. Length of terminal leaflet: Approximately 6.0 cm. Width of terminal leaflet: Approximately 4.4 cm. Length of lateral leaflet: Approximately 5.1 cm. Width of lateral leaflet: Approximately 3.3 cm.

Flowering description:

*Outdoor flowering habit.*—'Dapared' is freely flowering under outdoor growing conditions with substantially continuous blooming from spring through autumn and year round in greenhouse environment.

*Time to first flower.*—Approximately 8 weeks.

Inflorescence description:

*Appearance.*—Type: Composite. Arrangement: Terminal, arising from leaf axils on strong peduncles, positioned over the foliage. Disc and ray florets arranged acropetally on a capitulum. Persistent.

*Quantity per plant.*—Approximately 3 fully open at any one time.

*Lastingness of bloom.*—7–10 days.

*Shape/size.*—Hemispherical. Aspect: Facing upward or slightly outward. Diameter: Approximately 7.5 cm. Depth: Approximately 4.2 cm. Disc diameter: Approximately 1.1 cm. Receptical diameter: Approximately 8.8 mm. Receptical height/depth: Approximately 3.7 mm. Receptical color: 145A.

*Flower bud.*—Quantity per plant: Approximately 4 showing color at any one time. Rate of opening: Generally takes approximately 2 weeks for buds to progress from first color to fully open flower. Shape: Oblate. Length at first color: Approximately 1.9 cm. Width at first color: Approximately 1.8 cm. Texture: Glabrous. Color: 18C.

*Fragrance.*—None.

*Ray florets.*—Quantity: Approximately 67 per inflorescence. Shape: Elliptic, cupped. Apex: Emarginate with three tips. Base: Attenuate, fused to form tube. Margin: Entire. Length: Approximately 3.5 cm. Width: Approximately 1.7 cm. Texture: Glabrous. Color of upper surface when just open: 45A. Color of lower surface when just open: 179A. Color of upper surface when fully open: 44A. Color of lower surface when fully open: Closest to 179A with ridges of 1C.

*Disc florets.*—Quantity: Approximately 35. Shape: Cylindrical. Apex: 5 acute tips. Length: Approximately 1.2 cm. Diameter at apex: Approximately 2.4 mm. Diameter at base: Approximately 1.1 mm. Texture: Glabrous. Color: Transparent, closest to 6B.

*Peduncle.*—Strength: Strong. Aspect: Erect. Length: Approximately 3.3 cm. Diameter: Approximately 2.6 mm. Texture: Glabrous. Color: 144A.

*Phyllaries.*—Quantity: One per floret. Shape: Linear, slightly overlapping. Apex: Acute. Base: Truncate. Margin: Entire. Length of outermost phyllary: Approximately 1.6 cm. Width of outermost phyllary: Approximately 5.6 mm. Length of innermost phyllary: Approximately 1.2 cm. Width of innermost phyllary: Approximately 3.9 mm. Texture of upper and lower surfaces: Glabrous. Color of upper and lower surfaces: 145B with 143A at base.

*Secondary phyllaries.*—Quantity: Approximately 8. Shape: Rhomboidal. Apex: Acute. Base: Attenuate.

Margin: Entire. Length: Approximately 1.2 cm. Width: Approximately 5.4 mm. Texture of upper and lower surfaces: Glabrous. Color of upper and lower surfaces: 137A.

*Reproductive organs.*—Androecium — On disc florets. Stamen number: 5. Anther shape: Linear. Anther length: Approximately 4 mm. Anther color: 14A. Pollen amount: Abundant. Pollen color: 17A. Gynoecium — On disc and ray florets. Pistil length: Approximately 1.7 cm. Stigma length: 4 mm. Stigma color: 14B. Style length: 1.25 cm. Style color: 1B. Ovary length: 1.5 mm. Ovary color: 150D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Dapared', substantially as herein shown and described.

* * * * *